US008066666B2

(12) United States Patent
Kastenhofer

(10) Patent No.: US 8,066,666 B2
(45) **Date of Patent: *Nov. 29, 2011**

(54) MULTILAYER INTERVENTIONAL CATHETER

(75) Inventor: Gerhard Kastenhofer, Zurich (CH)

(73) Assignee: Schneider (Europe) A.G., Bulach (CH)

( * ) Notice: Subject to any disclaimer, the term of this patent is extended or adjusted under 35 U.S.C. 154(b) by 204 days.

This patent is subject to a terminal disclaimer.

(21) Appl. No.: 12/361,321

(22) Filed: Jan. 28, 2009

(65) Prior Publication Data

US 2009/0137954 A1 May 28, 2009

Related U.S. Application Data

(63) Continuation of application No. 10/697,613, filed on Oct. 29, 2003, now Pat. No. 7,485,108, which is a continuation of application No. 09/978,964, filed on Oct. 15, 2001, now Pat. No. 6,659,977, which is a continuation of application No. 08/845,569, filed on Apr. 25, 1997, now Pat. No. 6,319,228.

(30) Foreign Application Priority Data

Apr. 26, 1996 (EP) .................................... 96106578

(51) Int. Cl.
*A61M 29/00* (2006.01)

(52) U.S. Cl. ...................... 604/96.01; 604/264; 604/525

(58) Field of Classification Search .... 604/96.01–103.4, 604/525, 264, 523, 524; 428/36.91; 606/192, 606/194; 138/140–141, 145, 146, 149, 118; 156/242, 293, 244.11, 244.12, 294

See application file for complete search history.

(56) References Cited

U.S. PATENT DOCUMENTS 3,561,493 A 2/1971 Maillard et al.
3,618,614 A 11/1971 Flynn
3,695,921 A 10/1972 Shepherd et al.
3,814,137 A 6/1974 Martinez
3,890,976 A 6/1975 Bazell et al.
4,157,932 A 6/1979 Hirata
4,171,416 A 10/1979 Motegi et al.
4,211,741 A 7/1980 Ostoich
4,265,848 A 5/1981 Rüsch
4,282,876 A 8/1981 Flynn
4,323,071 A 4/1982 Simpson et al.
4,335,723 A 6/1982 Patel (Continued)

FOREIGN PATENT DOCUMENTS

CA 2078201 A1 12/1992

(Continued)

OTHER PUBLICATIONS

"Abrasion & Wear," Encyclopedia of Polymer Science and Engineering, vol. 1, A to Amorphous Polymers, A Wiley-Interscience Publication (1985) pp. 1-35.

(Continued)

*Primary Examiner* — Nicholas D Lucchesi
*Assistant Examiner* — Quynh-Nhu H Vu
(74) *Attorney, Agent, or Firm* — Seager, Tufte & Wickhem, LLC

(57) ABSTRACT

The catheter comprises a catheter tube formed of two superposed tubular layers of materials which differ from one another. A tubular mediator layer is arranged between the layers to provide an adhesive anchorage for the layers.

20 Claims, 3 Drawing Sheets

U.S. PATENT DOCUMENTS 4,413,989 A 11/1983 Schjeldahl et al.
4,596,563 A 6/1986 Pande
4,597,755 A 7/1986 Samson et al.
4,627,844 A 12/1986 Schmitt
4,629,650 A * 12/1986 Kataoka ........................ 428/213
4,636,346 A 1/1987 Gold et al.
4,646,719 A 3/1987 Neuman et al.
4,702,252 A 10/1987 Brooks et al.
4,707,389 A 11/1987 Ward
4,729,914 A 3/1988 Kliment et al.
4,744,366 A 5/1988 Jang
4,762,129 A 8/1988 Bonzel
4,763,654 A 8/1988 Jang
4,769,099 A 9/1988 Therriault et al.
4,775,371 A 10/1988 Mueller, Jr.
4,776,849 A 10/1988 Shinno et al.
4,782,834 A 11/1988 Maguire et al.
4,820,349 A 4/1989 Saab
4,863,449 A 9/1989 Therriault et al.
4,900,314 A 2/1990 Quackenbush
4,906,244 A 3/1990 Pinchuk et al.
4,921,483 A 5/1990 Wijay et al.
4,923,450 A 5/1990 Maeda et al.
4,940,179 A 7/1990 Soni
4,948,643 A 8/1990 Mueller
4,955,895 A 9/1990 Sugiyama et al.
4,960,410 A 10/1990 Pinchuk
4,976,690 A 12/1990 Solar et al.
4,976,720 A 12/1990 Machold et al.
4,981,478 A 1/1991 Evard et al.
4,994,018 A 2/1991 Saper
4,994,032 A 2/1991 Sugiyama et al.
4,994,047 A 2/1991 Walker et al.
5,006,119 A 4/1991 Acker et al.
5,026,377 A 6/1991 Burton et al.
5,035,694 A 7/1991 Kasprzyk et al.
5,041,089 A 8/1991 Mueller et al.
5,041,100 A 8/1991 Rowland et al.
5,047,045 A 9/1991 Arney et al.
5,059,269 A 10/1991 Hu et al.
5,063,018 A 11/1991 Fontirroche et al.
5,078,727 A 1/1992 Hannam et al.
5,085,649 A 2/1992 Flynn
5,100,381 A 3/1992 Burns
5,100,386 A 3/1992 Inoue
5,114,423 A 5/1992 Kasprzyk et al.
5,120,323 A 6/1992 Shockey et al.
5,147,315 A 9/1992 Weber
5,195,969 A 3/1993 Wang et al.
5,195,971 A 3/1993 Sirhan
5,221,270 A 6/1993 Parker
5,234,416 A 8/1993 Macaulay et al.
5,250,069 A 10/1993 Nobuyoshi et al.
5,254,090 A 10/1993 Lombardi et al.
5,267,959 A 12/1993 Forman
5,270,086 A 12/1993 Hamlin
5,272,012 A 12/1993 Opolski
5,279,560 A 1/1994 Morrill et al.
5,290,230 A 3/1994 Ainsworth et al.
5,290,306 A 3/1994 Trotta et al.
5,304,134 A 4/1994 Kraus et al.
5,338,299 A 8/1994 Barlow
5,344,402 A 9/1994 Crocker
5,348,536 A 9/1994 Young et al.
5,356,709 A 10/1994 Woo et al.
5,378,237 A 1/1995 Boussignac et al.
5,383,853 A 1/1995 Jung et al.
5,395,866 A 3/1995 Ross et al.
5,397,306 A 3/1995 Nobuyoshi et al.
5,403,292 A 4/1995 Ju
5,405,338 A 4/1995 Kranys
5,409,495 A 4/1995 Osborn
5,423,754 A 6/1995 Cornelius et al.
5,425,712 A 6/1995 Goodin
5,439,454 A 8/1995 Lo et al.
5,460,608 A 10/1995 Lodin et al.
5,478,320 A 12/1995 Trotta
5,484,444 A 1/1996 Braunschweiler et al.
5,499,973 A 3/1996 Saab
5,501,759 A 3/1996 Forman
5,514,236 A 5/1996 Avellanet et al.
5,527,281 A 6/1996 Haas
5,533,985 A 7/1996 Wang
5,538,510 A 7/1996 Fontirroche et al.
5,545,151 A 8/1996 O'Connor et al.
5,549,552 A 8/1996 Peters et al.
5,558,737 A 9/1996 Brown et al.
5,562,127 A 10/1996 Fanselow et al.
5,571,089 A 11/1996 Crocker
5,620,649 A 4/1997 Trotta
5,643,209 A 7/1997 Fugoso et al.
5,653,691 A 8/1997 Rupp et al.
5,676,659 A 10/1997 McGurk
5,728,063 A 3/1998 Preissman et al.
5,728,088 A 3/1998 Magruder et al.
5,733,400 A 3/1998 Gore et al.
5,749,852 A 5/1998 Schwab et al.
5,792,814 A 8/1998 Oishi et al.
5,797,877 A 8/1998 Hamilton et al.
5,820,594 A 10/1998 Fontirroche et al.
5,824,173 A 10/1998 Fontirroche et al.
5,837,313 A 11/1998 Ding et al.
5,843,032 A 12/1998 Kastenhofer
5,853,400 A 12/1998 Samson
5,961,765 A 10/1999 Kastenhofer
6,027,477 A 2/2000 Kastenhofer
6,165,166 A 12/2000 Samuelson et al.
6,319,228 B1 * 11/2001 Kastenhofer .............. 604/96.01
6,471,673 B1 10/2002 Kastenhofer
6,659,977 B2 * 12/2003 Kastenhofer .............. 604/96.01
7,485,108 B2 * 2/2009 Kastenhofer .............. 604/96.01

FOREIGN PATENT DOCUMENTS

EP 0 277 368 A1 8/1988
EP 0 279 959 A1 8/1988
EP 0 298 634 A1 1/1989
EP 0 351 687 A2 1/1990
EP 0 358 117 A2 3/1990
EP 0 380 102 A1 8/1990
EP 0 420 488 A1 4/1991
EP 0 436 501 A1 7/1991
EP 0 452 123 A1 10/1991
EP 0 456 342 A1 11/1991
EP 0 520 692 A1 12/1992
EP 0 530 201 B1 3/1993
EP 0 650 740 A1 5/1995
EP 0 669 142 A2 8/1995
EP 0 803 264 A1 10/1997
GB 2 130 093 A 5/1984
GB 2 209 121 A 5/1989
JP 2-234766 A 9/1990
JP 7-112029 A 5/1995
JP 7-178178 A 7/1995
WO WO 89/02763 A1 4/1989
WO WO 92/11893 A1 7/1992
WO WO 93/05842 A1 4/1993
WO WO 95/18647 A2 7/1995

OTHER PUBLICATIONS

"Asuka™ 2.9F OTW PTCA Balloon Catheter," Feb. 1994.
"Physical Constants of Important Polymers," Polymer Handbook, 2nd Edition, A Wiley-Interscience Publication (1975) pp. V-13 thru V-22.
"Physical Constants of Poly(Vinyl Chloride)," Polymer Handbook, 2nd Edition, A Wiley-Interscience Publication (1975) pp. V-41 thru V-50.
Bynel® Coextrudable Adhesive Resins Selector Guide (6 Sheets).
Chevron Chemical Company Technical Data Sheet Ethylene-Methyl Acrylate Copolymer EMAC SP 2260 (2 Sheets).
Chevron Chemical Company Technical Data Sheet Ethylene-Methyl Acrylate Copolymer EMAC 2205 (2 Sheets).
DSM Engineering Plastics Amitel®—Available Grade List (4 Sheets).
DuPont Hytrel® Polyester Elastomer Hytrel 7246 (2 Sheets).
Gaylord, Norman G. et al., "Compatibilizing Agents: Structure and Function in Polyblends," *J. Macromol. Sci-Chem.*, A26(8) (1989) pp. 1211-1229.
Gaylord, Norman G., "Maleation of Linear Low-Density Polyethylene by Reactive Processing," *Journal of Applied Polymer Science*, vol. 44, No. 11, Apr. 15, 1992, pp. 1941-1949.
Opti-Plast PTA Balloon Dilatation Catheters: for Peripheral Angioplasty (4 Sheets).
Petrothene® LM 6007-00 (1 Sheet).
Petrothene® LS 5060-00 (1 Sheet).
Plexar® PX 209 (2 Sheets).
Plexar® PX 360 (2 Sheets).
Plexar® Tie-Layer Resigns, Products, Applications, and Key Properties (3 Sheets).
Quantum Chemical Corporation Material Safety Data Sheet Plexar® (5 Sheets).

* cited by examiner 8
1
3
2
4
7
10
11
5
9
6
FIG—1

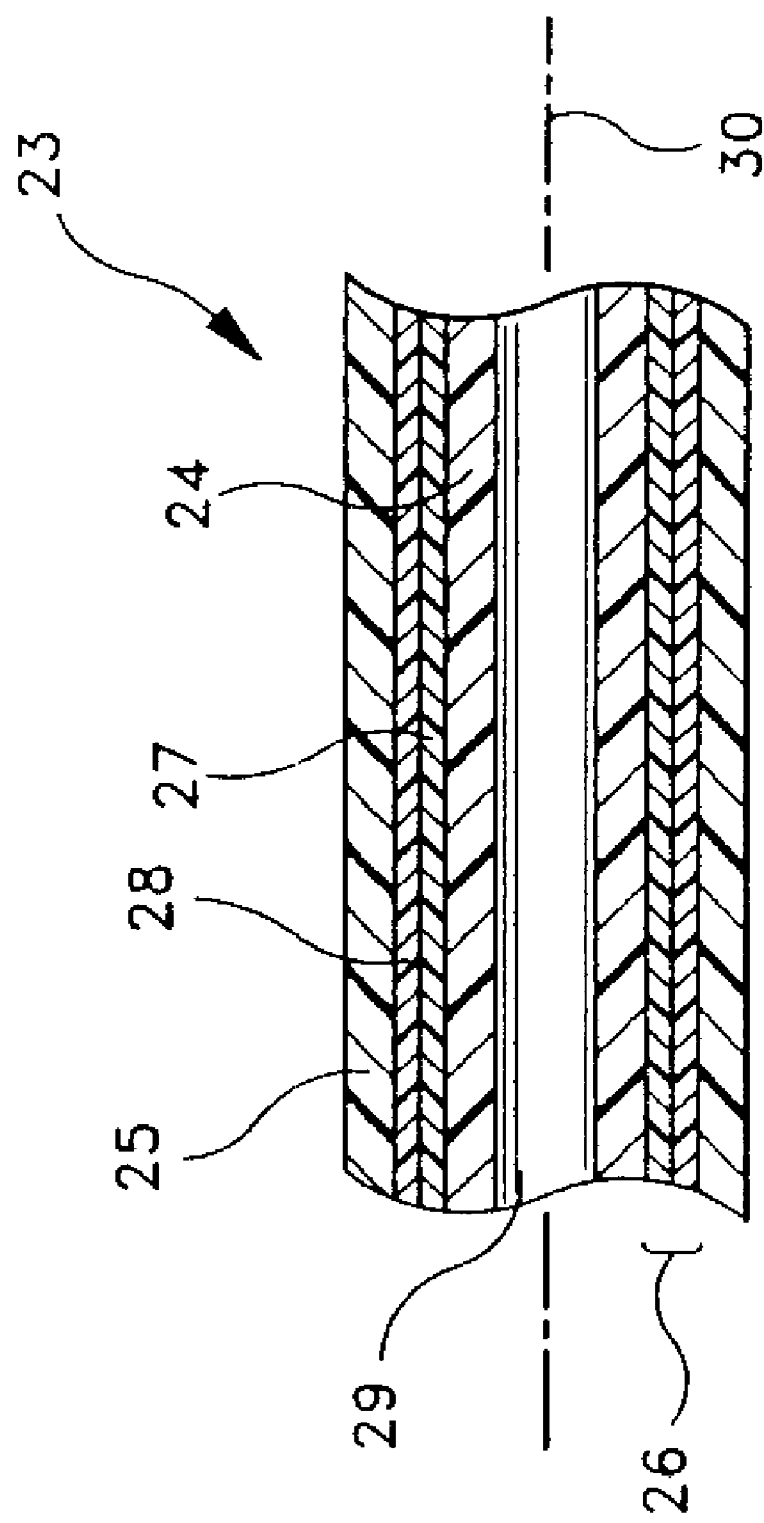
FIG—3

MULTILAYER INTERVENTIONAL CATHETER

CROSS-REFERENCE TO RELATED APPLICATIONS

This application is a continuation of pending U.S. application Ser. No. 10/697,613, filed Oct. 29, 2003; which is a continuation of U.S. application Ser. No. 09/978,964, filed Oct. 15, 2001, now U.S. Pat. No. 6,659,977; which is a continuation of U.S. application Ser. No. 08/845,569, filed Apr. 25, 1997, now U.S. Pat. No. 6,319,228; which claims priority to European Application No. 96106578.6, filed Apr. 26, 1996, the entire disclosures of which are all incorporated herein by reference.

BACKGROUND OF THE INVENTION

This invention relates to an interventional catheter comprising a catheter tube having two superposed layers of materials secured together and with mechanical properties differing from one another, a guidewire lumen in the catheter tube for the sliding fit of a guidewire, and a balloon with a distal end sealingly surrounding the catheter tube whereby the catheter tube has an inner layer forming the guidewire lumen and an outer layer forming an outer surface of the catheter tube.

Over the wire catheters have been widely used for interventions such as percutaneous transluminal cardiovascular angioplasty. A problem with these catheters is that the guidewire may clog into the guidewire lumen of the catheter, whereby the guidewire may follow the balloon upon withdrawal thereof after the inflation procedure thereby making it necessary to re-insert the guidewire into the treated area of the blood vessel for repositioning a balloon therein in case a second inflation is needed. A further problem is that the catheter has to achieve an acceptable compromise between the requirements of some stiffness to assure good pushability and some flexibility to assure kink resistance. In addition, the catheter has to permit safe attachment of the balloon to the catheter tube.

Monorail® technology, which provides for an entry of the guidewire distal of the balloon and an exit for the guidewire distal of the proximal end of the catheter tube, substantially reduces the risk of the guidewire clogging in the guidewire lumen because the length of frictional engagement between the guidewire and the guidewire lumen is strongly reduced. That is also of great help in the handling of balloon catheters for balloon exchange purposes. Though limited, the friction and clogging problem is, however, still existent.

Two layer catheter shafts have been developed. For example, the document WO 92/11893 describes an intra-aortic balloon apparatus comprising a hollow catheter in which is located an elongated member forming a central lumen extending out of the catheter at the distal end thereof. An aortic pumping balloon is positioned over the elongated member; the distal end of the balloon is bonded to a tip affixed to the distal end of the elongated member, and its proximal end is bonded to the distal end of the catheter. In order to achieve a balance of flexibility and remains and to avoid kinking, the elongated member is formed of an inner layer comprised of a soft elastomeric material to impart flexibility to the tubing and the outer layer is comprised of a hard plastic material to impart structural support to the elongated member. This balloon apparatus cannot be loaded with a guidewire and moved into tortuous vessels with the guidewire loaded inside the elongated member as the friction between guidewire and elongated member increases distinctively when the elongated member is shaped into curves. There would be therefore the risk that a spiral wound guidewire could be captured in the soft elastomeric plastic material of the inner layer of the elongated member. Although the outer layer of the elongated member that is coextruded onto the inner layer is formed of nylon, a material which is expected to be directly weldable to a wide variety of materials, this balloon apparatus cannot be introduced into narrow vessels or narrow stenoses, nor can it be passed through narrow punctures to enter the blood vessels. This is because of the relatively large profile of the folded balloon, due to the distal fixture of the balloon to the elongated member. The balloon is bonded to an intermediate tip element which in turn is bonded to the elongated member.

The document EP 0 650 740 A1 shows a catheter comprising a catheter tube having two superposed layers of materials secured in relation to one another and with mechanical properties differing from one another, a longitudinal lumen in the catheter tube for the sliding fit of a guidewire, and a balloon with a proximal end and a distal end, the distal end sealingly surrounding the catheter tube, whereby the catheter tube has an inner layer forming the longitudinal lumen and an outer layer forming the outer surface of the catheter tube. In this catheter, the inner layer is formed of a material with lower friction coefficient than the material forming the outer layer, whereby there is no more risk of having the guidewire clogging in the guidewire lumen of the catheter tube.

In terms of two layers catheter shafts, it has been observed that in practical use the adhesion of the two layers of material was not absolutely satisfactory. Although the coextrusion technology currently used for making such catheter shafts seems to involve close molecular interpenetration of the materials forming the superposed layers of the shaft, it has been possible to observe separation of the two layers, for example at the place of insertion of the shaft over the guidewire. Furthermore, tear test effected on such structures has shown that the two layers can separate under extreme conditions of stress on the shaft.

It is an object of this invention to propose an interventional balloon catheter avoiding the aforesaid drawbacks. A further object of the invention is an interventional catheter structure which is versatile and which provides a fully controllable and easy to manufacture assembly. Still a further object of the invention is an interventional low profile balloon catheter that can be safely operated on a guidewire and moved into tortuous vessels and other extreme conditions. Various multilayer catheters are known in the art. Reference is made to U.S. Pat. Nos. 4,627,844; 4,636,346; 5,403,292; 5,499,973; and 5,538,510.

All documents cited herein, including the foregoing, are incorporated herein by reference in their entireties for all purposes.

SUMMARY OF THE INVENTION

Accordingly, where the catheter comprises mediator layer means arranged between the inner layer and the outer layer for the adhesive anchorage of the layers thereto, securing of the inner layer and outer layer is strongly enhanced independently of their intrinsic capacity of adhesion to one another. The risk of a poor adhesion or the risk of a failure in the adhesion of the two layers to one another is eliminated. The inner and outer layers may be chosen for their most appropriate mechanical characteristics rather than for their capacity to adhere to one another. Because of the adhesive anchorage of the inner and outer layers on the mediator layer means, the risk of separation of the two layers upon insertion of the catheter tube over a guidewire is minimized. And the assembly of inner and outer layers is under control and the possibilities of changing the flexibility of the assembly are improved; due to the adhesive anchorage on the mediator layer means, rigidity of the assembly is enhanced with the same basic inner and outer layers, whereas flexibility of the assembly may be mastered by safely acting on the thickness of the inner and outer layers, with the resulting reduction in the profile of the catheter. As a result of the adhesive anchorage of the inner and outer layers on the mediator layer means the assembly behaves like a unit; accordingly, the assembly may be safely grabbed by the outer layer and tear tests are thus facilitated.

The inner and outer layers and the mediator layer means may be congruent in length, so that the catheter shaft can be produced in long tubes which may be cut at will to the appropriate length. Where the inner layer, the mediator layer means and the outer layer are coextruded, a catheter tube is formed in a continuous process avoiding the need of using a core in the inner layer.

Where the inner and outer layers are substantially transparent and the mediator layer means are contrasted with respect to the substantially transparent inner and outer layers, a visual control of the assembly is readily available to further improve the manufacture.

Where the mediator layer means have mechanical properties differing from the mechanical properties of the inner and outer layers a further step is achieved in the possibility of changing the lengthwise flexibility properties of the catheter.

When the inner layer is formed of a material with lower friction coefficient than the material forming the outer layer, there is no more risk of having the guidewire clogging or being captured in the guidewire lumen of the catheter tube. Withdrawal and re-positioning of the balloon catheter on a guidewire left in place at the site of treatment in the vessel system is rapid, safe and precise. Furthermore, the choice can be made for materials for the inner and outer layers having the most appropriate friction and kink resistance coefficients, while safe attachment of the balloon may be made at will on the outer layer which is chosen without being influenced by the friction properties of the inner layer.

The mediator layer means may be formed on the basis of a low density polyethylene to offer superior adhesion performance in a wide variety of configurations of the inner and outer layers and ease of processing on conventional fabrication equipment.

In a preferred form of the invention, the inner layer is made of a polyethylene or of a high density polyethylene, both of which assure an extremely low friction coefficient and an appropriate kink resistance coefficient. In another preferred form of the invention, the outer layer is made of a polyamid to assure easy welding of the balloon and a good stiffness at that level.

In sum, the invention relates to an interventional catheter comprising a catheter tube having two superposed layers of materials secured together and with mechanical properties differing from one another. A guidewire lumen is formed in the catheter tube for the sliding fit of a guidewire, and a balloon with a distal end sealingly surrounding the catheter tube. The catheter tube has an inner layer forming the guidewire lumen and an outer layer forming an outer surface of the catheter tube wherein it comprises mediator layer means arranged between the inner layer and the outer layer for the adhesive anchorage of the layers thereto. The inner and outer layers and the mediator layer means may be congruent in length. The inner layer, the mediator layer means, and the outer layer may be coextruded. The inner and outer layers may be substantially transparent and the mediator layer means may be contrasted with respect to the substantially transparent inner and outer layers. The mediator layer means may have mechanical properties differing from mechanical properties of the inner and outer layers. The inner layer may be formed of a material with lower friction coefficient than the material forming the outer layer. The mediator layer means may be formed on the basis of a low density polyethylene. The inner layer may be made of a polyethylene. The inner layer may be made of a high density polyethylene. The outer layer may be made of a polyamid.

These and other objects, features and advantages of the invention will become readily apparent from the following description with reference to the accompanying drawings which show, diagrammatically and by way of example only, preferred but still illustrative embodiments of the invention.

As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTION OF THE DRAWINGS

FIG. 3 is an enlarged cross-sectional view of a variant catheter embodiment of the invention.

DETAILED DESCRIPTION OF THE INVENTION

Figure 1:
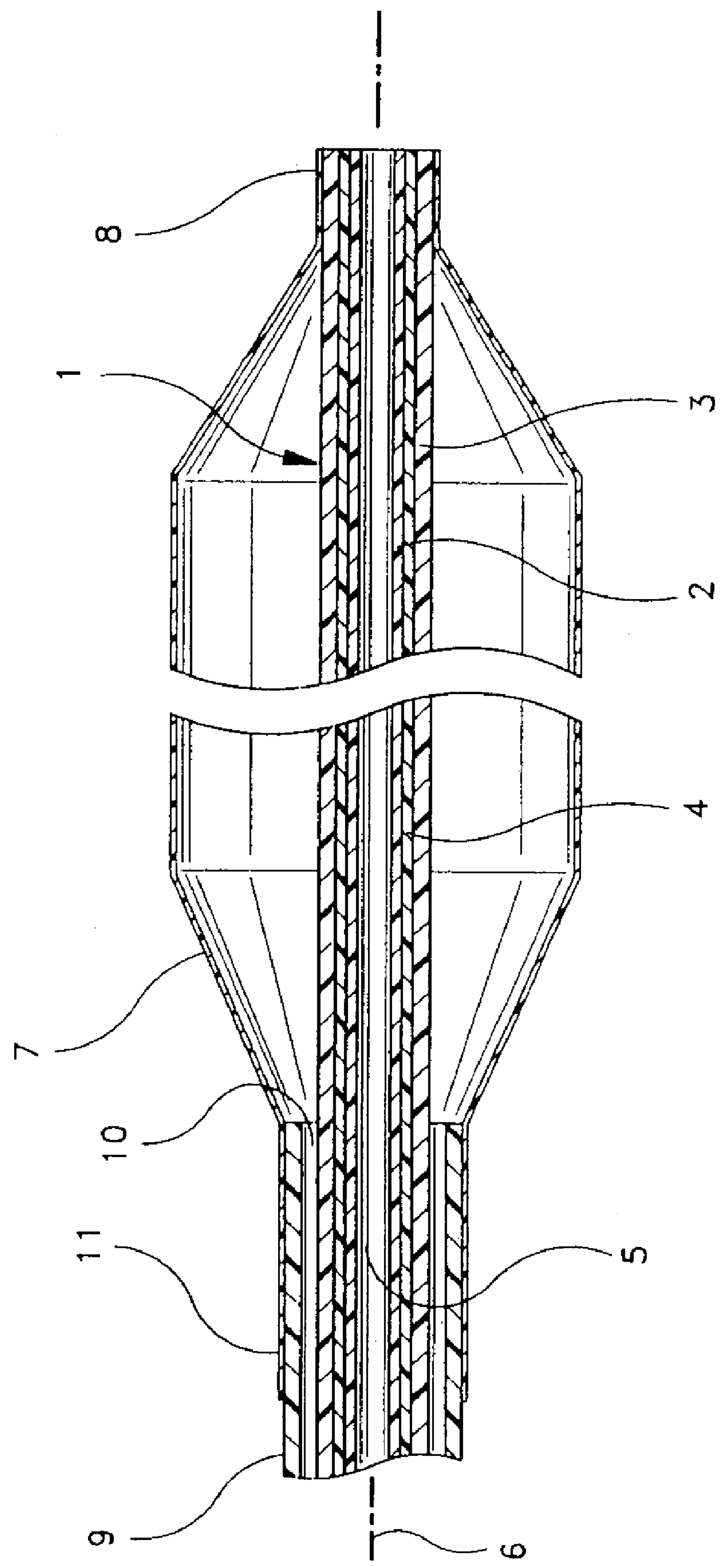
FIG. 1 is a longitudinal cross-sectional view of an over the wire balloon catheter embodying the invention.

The interventional catheter shown in FIG. 1 comprises a catheter tube 1 formed of two superposed tubular layers of materials 2 and 3 with a tubular mediator layer 4 arranged therebetween for the adhesive anchorage of the layers 2 and 3 onto the mediator layer 4.

The tubular layers 2, 3, and 4 extend all over the length of catheter tube 1, being thus congruent in length, and the assembly of layers forming the catheter tube 1 may be obtained by the known coextrusion technology, i.e., by extruding simultaneously the inner layer 2 with the mediator layer 4 and with the outer layer 3 thereover. Layers 2 and 3 have mechanical properties differing from one another and, preferably, mediator layer 4 also has mechanical properties differing from the mechanical properties of inner and outer layers 2 and 3.

Preferably, the inner layer 2 is formed of a material with lower friction coefficient than the material forming the outer layer 3. For example, the inner layer 2 may be formed of a polyethylene, preferably a high density polyethylene, whereas the outer layer 3 may be formed of a polyamid. The mediator layer 4 may be formed on the basis of a low density polyethylene.

Preferably, the inner and outer layers 2 and 3 are substantially transparent, whereas the mediator layer 4 is contrasted with respect to the substantially transparent inner and outer layers 2 and 3.

The catheter tube 1 has thus a longitudinal lumen 5 for the sliding fit of a guidewire exemplified by dotted line 6, which lumen 5 has a very low friction coefficient, lower than that of the outer layer 3, and a non-kinking capacity while the outer layer 3 forms an outer surface of the catheter tube 1 and is easily weldable to the materials commonly used for making balloons for angioplasty purposes and the like. And therebetween, the mediator layer 4 assures the best adhesive anchorage of inner and outer layers 2 and 3 thereto, the catheter tube 1 thus behaving as a unitary element with differentiating properties at its inner and outer levels.

Over the distal portion of the catheter tube 1 is positioned a balloon 7 the distal end 8 of which sealingly surrounds the outer layer 3 of catheter tube 1, for example by welding.

A tube 9 is arranged over the catheter tube 1, at a radial distance thereof, thus defining an inflation lumen 10 for the balloon 7. The proximal end 11 of the balloon 7 is welded onto the distal end of tube 9.

Figure 2:
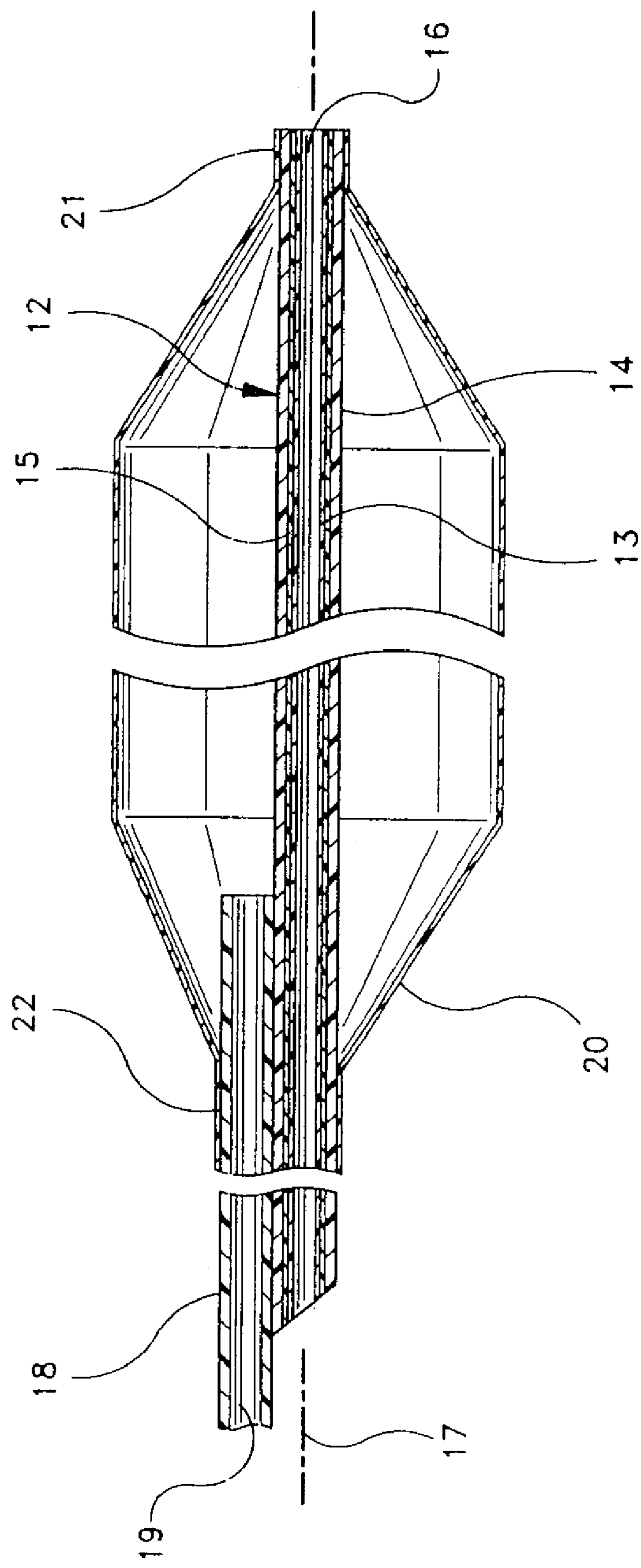
FIG. 2 is a longitudinal cross-sectional view of a Monorail® balloon catheter embodying the invention.

The interventional catheter shown in FIG. 2 also comprises a catheter tube 12 having two superposed tubular layers of materials 13 and 14 with a tubular mediator layer 15 arranged therebetween for adhesive anchorage of the layers 13 and 14 onto the mediator layer 15.

The tubular layers 13, 14 and 15 extend all over the catheter tube 12 and the assembly of layers forming the catheter tube 12 may also be obtained by the known coextrusion technology whereby inner tubular layer 13 is extruded simultaneously with the mediator layer 15 and the outer layer 14 thereover. Layers 13 and 14 have mechanical properties differing from one another and, preferably, mediator layer 15 also has mechanical properties differing from the mechanical properties of inner and outer layers 13 and 14.

Preferably the inner layer 13 is made of a material with lower friction coefficient than the material forming the outer layer 14. For example, inner layer 13 may be formed of a polyethylene, preferably a high density polyethylene, whereas the outer layer 14 may be made of a polyamid. The mediator layer 15 may be formed on the basis of a low density polyethylene.

Preferably the inner and outer layers 13 and 14 are substantially transparent and the mediator layer 15 is contrasted with respect to the substantially transparent inner and outer layers 13 and 14.

The catheter tube 12 has thus a longitudinal lumen 16 for the sliding fit of a guidewire exemplified by dotted line 17, which lumen 16 has a very low friction coefficient, lower than that of the outer layer 14 and with a non-kinking capacity, whereas outer layer 14 forms an outer surface of the catheter tube 12 and is easily weldable to the materials currently used for making angioplasty balloons. And therebetween, the mediator layer 15 also assures superior adhesive anchorage for inner and outer layers 13 and 14, the catheter tube 12 acting as a unit with different properties at its inner and outer levels.

A tube 18 is affixed, for example welded, in parallel relationship to the proximal portion of catheter tube 12, and this tube 18 extends proximally of the catheter tube 12. The tube 18 defines an inflation lumen 19 for a balloon 20 the distal end 21 of which sealingly surrounds the outer layer 14 of catheter tube 12, for example by welding. The proximal end 22 of balloon 20 sealingly surrounds a proximal portion of the catheter tube 12 and a distal portion of tube 18, whereby the proximal portion of catheter tube 12 extends proximally out of the balloon 20 and the distal portion of tube 18 extends within the balloon 20.

Variants are readily available. For example, the mediator layer may be made of two superposed tubular layers of materials which differ from one another in order to respectively provide superior adhesive anchorage for the inner and outer layers while assuring total adhesive anchorage between them. This configuration is advantageous for example to match particular flexibility requirements for the catheter tube or to assume adhesive anchorage conditions which would be otherwise difficult for the inner and outer layers.

FIG. 3 shows such a configuration where the catheter tube 23 is formed of two superposed tubular layers of materials 24 and 25 with a tubular mediator layer 26 arranged therebetween and formed of two superposed adhesively anchored tubular layers 27 and 28, layer 27 being for adhesive anchorage of inner layer 24 and layer 28 for adhesive anchorage of outer layer 25. Within inner layer 24 is the guidewire lumen 29 for the sliding fit of a guidewire exemplified by dotted line 30.

It will be evident from considerations of the foregoing that the Multilayer Interventional Catheter is now available, and may be constructed using a number of methods and materials, in a wide variety of sizes and styles for the greater efficiency and convenience of a user.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

I claim:

1. A catheter comprising:

an elongate tube including a tubular wall of a plurality of coextruded layers of polymeric material, including a first layer of a first polymeric material, a second layer of a second polymeric material located exterior of the first layer, and a third layer of a third polymeric material located interior of the first layer;

wherein the first polymeric material comprises low-density polyethylene having mechanical properties differing from each of the second polymeric material and the third polymeric material;

wherein the first layer has an inner surface adhered to an outer surface of the third layer, and the first layer has an outer surface adhered to an inner surface of the second layer; and a balloon surrounding a distal portion of the elongate tube and sealingly bonded to an outer surface of the elongate tube.

2. The catheter of claim 1, wherein the second layer is not in direct contact with the third layer.

3. The catheter of claim 1, wherein the first layer and the second layer are congruent in length.

4. The catheter of claim 1, wherein the first layer and the third layer are congruent in length.

5. The catheter of claim 1, wherein the first layer, the second layer and the third layer are congruent in length.

6. The catheter of claim 1, wherein the third layer defines a lumen of the elongate tube.

7. The catheter of claim 6, wherein the third layer comprises high-density polyethylene.

8. The catheter of claim 7, wherein the second layer comprises polyamide.

9. The catheter of claim 8, wherein the second layer forms the outer surface of the elongate tube.

10. A catheter comprising:

a first elongate tube having a lumen extending therethrough;

a second elongate tube disposed in the lumen of the first elongate tube, the second elongate tube including a tubular wall of a plurality of coextruded layers of polymeric material, including:

i) a first layer of a first polymeric material comprising low-density polyethylene;

ii) a second layer located exterior to the first layer; the second layer comprising a second polymeric material having mechanical properties differing from the first polymeric material;

iii) a third layer located interior of the first layer, the third layer comprising a third polymeric material having mechanical properties differing from the first polymeric material;

wherein the second polymeric material has a coefficient of friction which is greater than a coefficient of friction of the third polymeric material; and a balloon having a proximal portion sealingly surrounding the first elongate tube and distal portion sealingly surrounding the second elongate tube.

11. The catheter of claim 10, wherein the second layer is not in direct contact with the third layer.

12. The catheter of claim 10, wherein the second layer and the third layer are congruent in length.

13. The catheter of claim 10, wherein the third layer defines a lumen of the second elongate tube.

14. The catheter of claim 13, wherein the second layer forms an outer surface of the second elongate tube.

15. The catheter of claim 14, wherein the third layer comprises high-density polyethylene.

16. A catheter comprising:

a multi-layer coextruded tubular member including a first layer of a first polymeric material, a second layer of a second polymeric material located exterior of the first layer, and a third layer of a third polymeric material located interior of the first layer, the first layer being adhered to an outer surface of the third layer, and the first layer being adhered to an inner surface of the second layer;

wherein the first polymeric material comprises low-density polyethylene and the third polymeric material comprises high-density polyethylene.

17. The catheter of claim 16, wherein the second polymeric material comprises polyamide.

18. The catheter of claim 16, wherein the third layer defines a lumen of the multi-layer coextruded tubular member.

19. The catheter of claim 16, further comprising an outer tubular member extending over a portion of the multi-layer coextruded tubular member such that a lumen is defined between an outer surface of the multi-layer coextruded tubular member and an inner surface of the outer tubular member.

20. The catheter of claim 19, further comprising a balloon, wherein a proximal portion of the balloon sealingly surrounds the outer tubular member and a distal portion of the balloon sealingly surrounds the multi-layer coextruded tubular member.

* * * * *